(12) United States Patent
Nakagawa et al.

(10) Patent No.: US 6,686,453 B1
(45) Date of Patent: Feb. 3, 2004

(54) ANTIFUCOIDAN ANTIBODY

(75) Inventors: Kazuo Nakagawa, Otsu (JP); Fumitsugu Hino, Kusatsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 122 days.

(21) Appl. No.: 10/009,597

(22) PCT Filed: Jun. 7, 2000

(86) PCT No.: PCT/JP00/03679

§ 371 (c)(1), (2), (4) Date: Dec. 11, 2001

(87) PCT Pub. No.: WO00/77049

PCT Pub. Date: Dec. 21, 2000

(30) Foreign Application Priority Data

Jun. 11, 1999 (JP) ............................. 11/165191

(51) Int. Cl.[7] ..................... C07K 16/00; C12P 21/08
(52) U.S. Cl. ................. 530/388.1; 530/388.2; 530/388.4
(58) Field of Search ............. 530/387.1, 387.5, 530/388.1, 388.2, 391.1, 388.4

(56) References Cited

FOREIGN PATENT DOCUMENTS

| EP | 0 870 771 A1 | 10/1998 |
| EP | 0 919 237 A1 | 6/1999 |
| JP | 10-165184 A | 6/1998 |
| WO | 87/04186 | * 7/1987 |
| WO | 99/41288 | * 8/1999 |

* cited by examiner

*Primary Examiner*—Mark Navarro
(74) *Attorney, Agent, or Firm*—Browdy and Neimark

(57) ABSTRACT

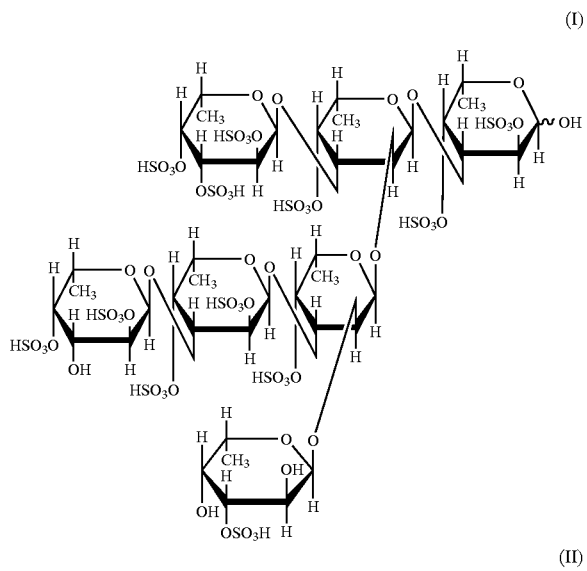

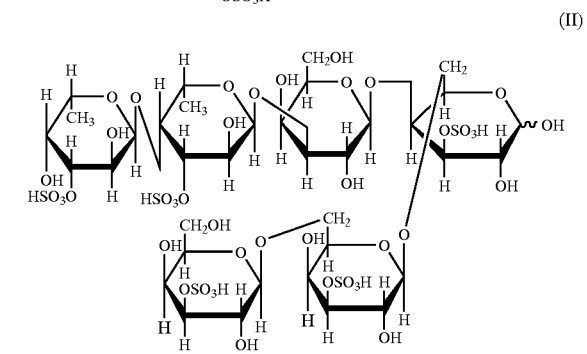

An antifucoidan antibody recognizing the compound represented by formula (I) or (II).

2 Claims, 1 Drawing Sheet

ANTIFUCOIDAN ANTIBODY

REFERENCE TO RELATED APPLICATIONS

The present application is the national stage under 35 U.S.C. §371 of international application PCT/JP00/03679, filed Jun. 7, 2000 which designated the United States, and which application was not published in the English language.

TECHNICAL FIELD

The present invention relates to an antibody that recognizes the structure of a physiologically active polysaccharide, fucoidan, which is useful for the functional study and the structural analysis of fucoidan.

BACKGROUND ART

Fucoidan is a polysaccharide that contains sulfated fucose in its molecule. Fucoidan that contains substantially no uronic acid and contains fucose as the main component of its constituting saccharides, and fucoidan that contains uronic acid and contains fucose and mannose as its constituting saccharides are known.

The present inventors prepared fucoidan that contains substantially no uronic acid and contains fucose as the main component of its constituting saccharides, i.e., sulfated-fucose-containing polysaccharide-F (hereinafter referred to as F-fucoidan), and fucoidan that contains uronic acid, i.e., sulfated-fucose-containing polysaccharide-U (hereinafter referred to as U-fucoidan) from *Kjellmaniella crassifolia* (see WO 97/26896).

Known physiological activities of fucoidan include an apoptosis-inducing activity, an antiproliferation activity against cancer, an activity of inhibiting cancer metastasis, an anticoagulant activity and an antiviral activity. Therefore, it is expected that fucoidan would be developed for medical use. In addition, fucoidan has an excellent function as a material for cosmetics.

Thus, it is desired to further analyze the structure and the physiological functions of fucoidan.

OBJECTS OF THE INVENTION

The main object of the present invention is to provide an antibody that specifically recognizes the structure of fucoidan, which antibody is useful for the structural analysis of fucoidan and the investigation of relationship between the structure and the physiological functions.

SUMMARY OF THE INVENTION

The present inventors have successfully created cells that produce antibodies that recognize the structure of fucoidan by immunizing a host with fucoidan derived from *Kjellmaniella crassifolia* as an antigen. Thus, the present invention has been completed.

Accordingly, the present invention provides an antifucoidan antibody that recognizes the compound of formula (I) or (II):

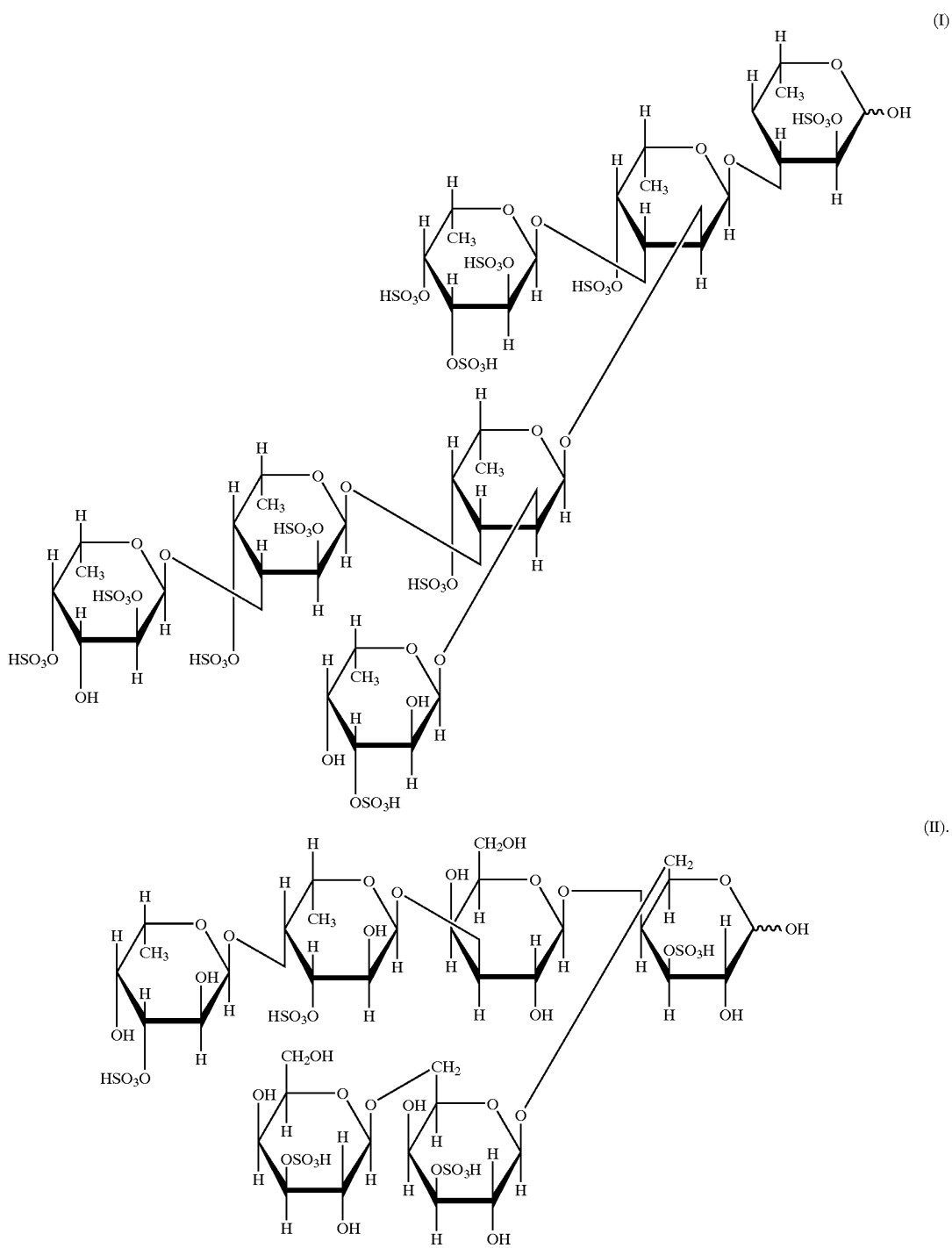

Furthermore, the present invention provides a carrier onto which said anti-fucoidan antibody is immobilized.

DETAILED DESCRIPTION OF THE INVENTION

Figure 1:
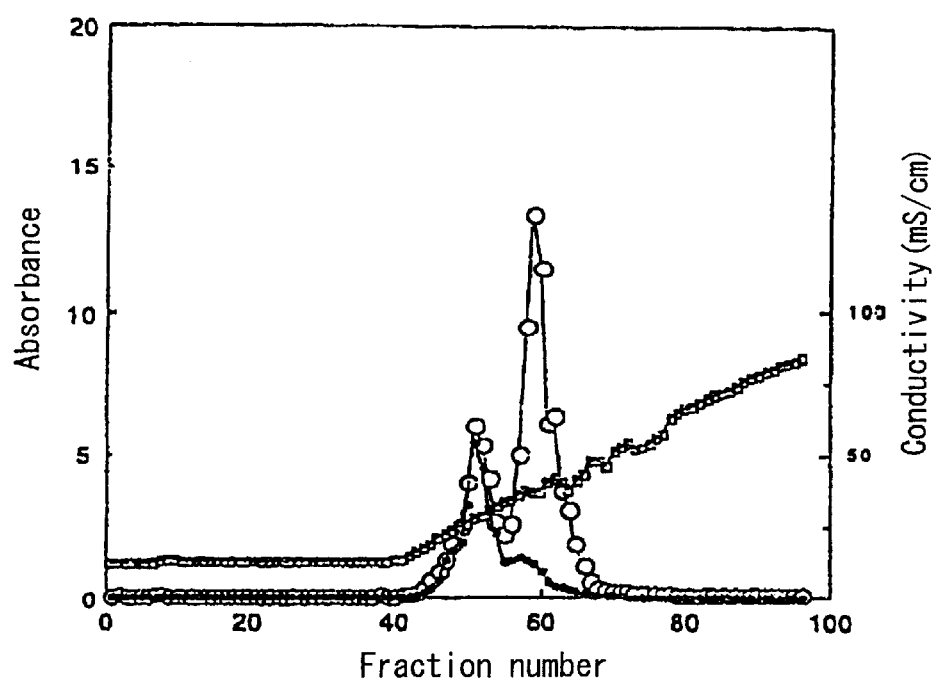
FIG. 1: a figure that illustrates the elution pattern of fucoidan derived from *Kjellmaniella crassifolia* from DEAE-Cellulofine A-800 column.

Fucoidan derived from *Kjellmaniella crassifolia*, which is to be used as an antigen for the preparation of the antibody of the present invention, can be prepared as described in WO 97/26896. Specifically, it can be prepared as described in Referential Example 1-(1). Also, U-fucoidan and F-fucoidan can be prepared as described in this publication. Specifically, they can be prepared as described in Referential Example 1-(2).

The compound of formula (I) can be prepared as described in WO 99/41288. Specifically, it can be prepared as described in Referential Example 2.

The compound of formula (II) can be prepared as described in WO 96/34004. Specifically, it can be prepared as described in Referential Example 3.

The compound of formula (I) is a smaller molecule generated from F-fucoidan by the action of the F-fucoidan-degrading enzyme produced by Alteromonas sp. SN-1009 (FERM BP-5747). F-fucoidan has a structure in which the compound of formula (I) as a constituting unit is repeated.

The compound of formula (II) is a smaller molecule generated from fucoidan by the action of the fucoidan-degrading enzyme produced by Flavobacterium sp. SA-0082 (FERM BP-5402).

The anti-fucoidan antibody of the present invention may be a polyclonal antibody or it may be prepared as a monoclonal antibody as long as it recognizes the compound of formula (I) or (II). Such a monoclonal antibody is produced according to a so-called cell fusion method. Specifically, the monoclonal antibody is produced as follows. Hybridomas are formed by fusing antibody-producing cells with myeloma cells. The hybridomas are cloned. A clone that produces an antibody specific to the compound of formula (I) or (II) is then selected.

For example, B lymphocytes in spleen cells or lymph node cells from an animal immunized with fucoidan derived from *Kjellmaniella crassifolia* can be used as antibody-producing cells. Animals to be immunized are exemplified by mice, rats, horses, goats and rabbits.

Fucoidan derived from *Kjellmaniella crassifolia*, U-fucoidan, F-fucoidan or the like can be utilized as an antigen. Such an antigen is mixed with Freund's adjuvant and used to immunize an animal.

Immunization is carried out by subcutaneously, intramuscularly or intraperitoneally administering 20 to 200 µg/dose of an antigen to an animal once in 2 to 3 weeks for 3 to 7 weeks. Antibody-producing cells are collected from the immunized animal about 3 to 5 days after the final immunization.

As myeloma cells, those derived from a mouse, a rat, a human or the like are used. Cell fusion is carried out, for example, according to the method as described in Nature, 256:495 (1975) or a modification thereof. In the method, cell fusion is carried out by a reaction at a temperature of 30 to 40° C. for about 1 to 3 minutes using 30 to 50% polyethylene glycol having a molecular weight of 1000 to 4000.

Hybridomas obtained by the cell fusion are subjected to screening using an enzyme immunoassay or the like. The thus-obtained antibody-producing hybridoma is subjected to cloning. Specifically, clones are obtained by cloning the hybridoma, for example, by limiting dilution. The clones are then subjected to screening using enzyme immunoassay or the like for a clone that produces the monoclonal antibody of interest. For example, the selected clone is intraperitoneally implanted into a BALB/c mouse that has received pristane (2,6,10,14-tetramethylpentadecane). Ascites containing the monoclonal antibody at a high concentration is collected 10 to 14 days after the implantation. The monoclonal antibody is readily recovered from the ascites by applying known methods for purifying antibodies such as ammonium sulfate fractionation, polyethylene glycol fractionation, ion exchange chromatography and gel chromatography.

The antibody of the present invention is not limited to specific one as long as it can be prepared as described above. The antibody is exemplified by the anti-fucoidan antibody that is produced by a hybridoma GFD G-28 (FERM BP-7173), which recognizes the compound of formula (I) and does not recognize the compound of formula (II) (this antibody is referred to as GFDG-28 hereinafter), or the anti-fucoidan antibody that is produced by a hybridoma GFD 2-9C (FERM BP-7174), which does not recognize the compound of formula (I) and recognizes the compound of formula (II) (this antibody is referred to as GFD2-9C hereinafter).

Furthermore, by immobilizing the antibody of the present invention onto a carrier and using it as a carrier for adsorption, the following can be distinguished: the compound of formula (I) or (II), a polysaccharide containing the compound of formula (I) or (II), or a polysaccharide having the compound of formula (I) or (II) as its constituting unit. Known methods can be used to immobilize the antibody of the present invention onto a carrier. The material of the carrier to be used for immobilization can be appropriately selected depending on the object or the method from, for example, the group consisting of polysaccharides such as agarose, cellulose and dextran, synthetic polymer such as polyacrylamide, acrylic acid polymer, stylene divinylbenzen polymer and polymethacrylate, and inorganic polymer such as silica gel and glass.

GFDG-28 recognizes F-fucoidan. Thus, it can be used to measure F-fucoidan. Furthermore, it can be used to measure the compound of formula (I) in a sandwich method. The recognition site is considered to be the fucose-2-sulfate site.

Such an antibody is useful for measuring fucoidan while distinguishing its type. For example, it can be used to measure fucoidan derived from *Kjellmaniella crassifolia*.

The antibody obtained as described above is very useful for investigating the relationship between the structure and the physiological activities of fucoidan. Furthermore, the antibody is very useful for specifically and precisely measuring the concentration of a fucoidan-derived material in a living body, for example in serum, plasma or urine.

For these purposes, the monoclonal antibody itself or a fragment thereof that has the corresponding immunological properties such as a Fab fragment can be used. The antibodies of the present invention include antibodies or fragments thereof produced by genetic engineering.

EXAMPLES

The following Examples illustrate the present invention in more detail, but are not to be construed to limit the scope thereof.

Referential Example 1

(1) *Kjellmaniella crassifolia* was dried extensively. 20 kg of the dried product was ground using a pulverizer Jiyu Mill (Nara Machinery).

7.3 kg of calcium chloride dihydrate (Nippon Soda) was dissolved in 900 l of tap water. 20 kg of the ground *Kjellmaniella crassifolia* was mixed with the solution. The temperature of the mixture was elevated from 12° C. to 90° C. for 40 minutes by blowing steam into the mixture. The mixture was incubated at 90 to 95° C. for 1 hour while stirring and then cooled to obtain 1100 l of a cooled product.

The cooled product was subjected to solid-liquid separation using a solid-liquid separator (type CNA, Westfalier Separator) to prepare about 900 l of a supernatant.

360 l of the supernatant was concentrated to a volume of 20 l using FE10-FC-FUS0382 (fractionation molecular weight of 30,000, Daicel). 20 l of tap water was then added to the concentrate. The resulting mixture was concentrated to a volume of 20 l using FE10-FC-FUS0382 again. This procedure was repeated five times to desalt the mixture. Thus, 25 l of an extract was prepared from *Kjellmaniella crassifolia*.

1 l of the extract was lyophilized to obtain 13 g of dried fucoidan derived from *Kjellmaniella crassifolia*.

(2) 7 g of the dried fucoidan as described in Referential Example 1-(1) was dissolved in 700 ml of 20 mM imidazole buffer (pH 8.0) containing 50 mM sodium chloride and 10% ethanol. Insoluble substances were removed by centrifugation. DEAE-Cellulofine A-800 column ($\phi$11.4 cm×48 cm) (Seikagaku Corporation) was equilibrated with the same buffer. A supernatant obtained by the centrifugation was applied to the column. The column was washed with the same buffer. Elution was carried out using a gradient of sodium chloride concentration from 50 mM to 1.95 M. Eluate was collected at the rate of 250 ml per fraction. Total sugar and uronic acid content were determined according to the phenol-sulfuric acid method and the carbazole-sulfuric acid method. Fraction numbers 43 to 55 and fraction numbers 56 to 67 were collected. These fractions were desalted by electrodialysis and then lyophilized. Then, a fraction containing 1.21 g of U-fucoidan and a fraction containing 2.64 g of F-fucoidan were prepared from the fraction numbers 43 to 55 and the fraction numbers 56 to 67, respectively.

FIG. 1 illustrates the elution pattern of fucoidan derived from *Kjellmaniella crassifolia* from DEAE-Cellulofine A-800 column. In FIG. 1, the vertical axis represents the absorbance at 530 nm as measured according to the carbazole-sulfuric acid method (closed circles), the absorbance at 480 nm as measured according to the phenol-sulfuric acid method (open circles) and the conductivity (mS/cm, open squares). The horizontal axis represents the fraction number.

Referential Example 2

(1) Alteromonas sp. SN-1009 (FERM BP-5747) was inoculated into 600 ml of a medium consisting of artificial seawater (Jamarin Laboratory) containing 0.25% glucose, 1.0% peptone and 0.05% yeast extract (pH 8.2) which had been sterilized at 120° C. for 20 minutes in a 2 l Erlenmeyer's flask, and incubated at 25° C. for 26 hours to prepare a seed culture. 20 l of a medium consisting of artificial seawater (Jamarin Laboratory) containing 1.0% peptone, 0.02% yeast extract, 0.2% fucoidan prepared as described in Referential Example 2-(2) below and 0.01% antifoaming agent (KM70, Shin-Etsu Chemical) (pH 8.0) was placed in a 30 l jar fermentor and sterilized at 120° C. for 20 minutes. After cooling, 600 ml of the seed culture was inoculated into the medium and incubated at 24° C. for 24 hours with aeration at 10 l/min. and stirring at 250 rpm. After incubation, the culture was centrifuged to obtain a culture supernatant. The culture supernatant was concentrated using an ultrafiltration instrument equipped with hollow fibers having an exclusion molecular weight of 10,000, and subjected to salting out with 85%-saturated ammonium sulfate. The resulting precipitate was collected by centrifugation and extensively dialyzed against 20 mM Tris-hydrochloride buffer (pH 8.2) containing artificial seawater at a 1/10 concentration to prepare 600 ml of a solution of F-fucoidan-degrading enzyme which selectively acts on fucoidan.

(2) 2 kg of dried *Kjellmaniella crassifolia* was ground using a cutter mill (Masuko Sangyo) equipped with a screen having a mesh of diameter size of 1 mm. The resulting chips of *Kjellmaniella crassifolia* were suspended in 20 l of 80% ethanol. The suspension was stirred at 25° C. for 3 hours, and filtrated through a filter paper. The resulting residue was extensively washed and suspended in 40 l of 20 mM sodium phosphate buffer (pH 6.5) containing 50 mM sodium chloride which was heated at 95° C. The suspension was treated at 95° C. for 2 hours while stirring at intervals to extract fucoidan.

Substances suspended in the extract was filtrated to prepare a filtrate. The residue was washed with 3.5 l of 100 mM sodium chloride to obtain an additional filtrate.

The filtrates were combined together and cooled down to 30° C. 3000 U of alginate lyase (Nagase Biochemicals) was added thereto. 4 l of ethanol was further added. The mixture was stirred at 25° C. for 24 hours. A supernatant obtained by centrifuging the mixture was concentrated to a volume of 4 l using an ultrafiltration instrument equipped with hollow fibers having an exclusion molecular weight of 100,000. The ultrafiltration was continues using 100 mM sodium chloride containing 10% ethanol until no coloring substance became undetectable in the filtrate.

A precipitate generated in the retentate was removed by centrifugation. The supernatant was cooled down to 5° C. The pH was adjusted to 2.0 with 0.5 N hydrochloric acid. The resulting precipitate consisting of proteins and the like was removed by centrifugation. The pH of the thus-obtained supernatant was immediately adjusted to 8.0 with 1 N sodium hydroxide.

The solvent was completely substituted with 20 mM sodium chloride (pH 8.0) by ultrafiltration using an ultrafiltration instrument equipped with hollow fibers having an exclusion molecular weight of 100,000. The pH was adjusted to 8.0 again. After centrifugation, lyophilization was carried out to prepare about 95 g of fucoidan.

(3) 2 kg of dried *Kjellmaniella crassifolia* was ground using a cutter mill equipped with a screen having a mesh of diameter size of 1 mm. The resulting chips of *Kjellmaniella crassifolia* were suspended in 20 l of 80% ethanol. The suspension was stirred at 25° C. for 3 hours, and filtrated through a filter paper. The resulting residue was extensively washed and suspended in 20 l of a buffer (pH 8.2) containing 30 ml of the F-fucoidan-degrading enzyme solution prepared in Referential Example 2-(1), 10% ethanol, 100 mM sodium chloride, 50 mM calcium chloride and 50 mM imidazole. The suspension was stirred at 25° C. for 48 hours. The suspension was filtrated through a 32 $\mu$m stainless steel mesh. The residue was washed with 10% ethanol containing 50 mM calcium chloride. The residue was suspended in 10 l of 10% ethanol containing 50 mM calcium chloride. The suspension was stirred for 3 hours, filtrated through the stainless steel mesh and washed. The residue was suspended in the same manner. The suspension was stirred for 16 hours, filtrated through the 32 $\mu$m stainless steel mesh and washed.

The filtrates and the washing solutions obtained as described above were combined, and subjected to ultrafiltration using a ultrafiltration instrument equipped with hollow fibers having an exclusion molecular weight of 3000 to separate a filtrate from a retentate.

The filtrate was concentrated to a volume of about 3 l using a rotary evaporator. The concentrate was then centrifuged to obtain a supernatant. The supernatant was desalted using an electrodialysis instrument equipped with a membrane having an exclusion molecular weight of 300. Calcium acetate was added to the solution at a final concentration of 0.1 M. The resulting precipitate was removed by centrifugation. The thus-obtained supernatant was applied to DEAE-Cellulofine column (resin volume: 4 l) equilibrated with 50 mM calcium acetate. After extensively washing with 50 mM calcium acetate and 50 mM sodium chloride, elution was carried out using a gradient of sodium chloride concentration from 50 mM to 800 mM. Eluate was collected at the rate of 500 ml per fraction. When the collected fractions were analyzed using cellulose acetate membrane electrophoresis (Analytical Biochemistry, 37:197–202 (1970)), whereupon it was found that fucoidan eluted using a sodium chloride concentration of about 0.4 M (around fraction number 63) was homogeneous.

Then, the solution contained in the fraction number 63 was concentrated to a volume of 150 ml. Sodium chloride was added thereto at a final concentration of 4 M. The mixture was applied to Phenyl-Cellulofine column (resin volume: 200 ml) equilibrated with 4 M sodium chloride. The column was extensively washed with 4 M sodium chloride. Fractions containing non-adsorptive degradation products from fucoidan were collected and desalted using an electrodialysis instrument equipped with a membrane having an exclusion molecular weight of 300 to obtain 505 ml of a desalted solution.

40 ml of the desalted solution was applied to Cellulofine GCL-90 column (4.1 cm×87 cm) (Seikagaku Corporation) equilibrated with 0.2 M sodium chloride containing 10% ethanol for gel filtration. Eluate was collected at the rate of 9.2 ml per fraction.

An analysis of total saccharide amount was carried out for all fractions according to the phenol-sulfuric acid method (Analytical Chemistry, 28:350 (1956)).

As a result, the degradation product from fucoidan formed a single peak. Fraction numbers 63 to 70 centered in the peak were collected, desalted using an electrodialysis instrument equipped with a membrane having an exclusion molecular weight of 300 and lyophilized to obtain 112 mg of a dried product of the compound of formula (I) (hereinafter simply referred to as 7-12s).

Referential Example 3

(1) Flavobacterium sp. SA-0082 (FERM BP-5402) was inoculated into 600 ml of a medium consisting of artificial seawater (Jamarin Laboratory) containing 0.1% glucose, 1.0% peptone and 0.05% yeast extract (pH 7.5) which had been sterilized at 120° C. for 20 minutes in a 2 l Erlenmeyer's flask, and incubated at 24° C. for 20 hours to prepare a seed culture. 20 l of a medium consisting of artificial seawater (Jamarin Laboratory) containing 0.3% fucoidan derived from Kjellmaniella crassifolia as described in Referential Example 2-(2), 0.5% peptone, 0.01% yeast extract and 0.01% antifoaming agent (KM70, Shin-Etsu Chemical) (pH 7.5) was placed in a 30 l jar fermentor and sterilized at 120° C. for 20 minutes. After cooling, 600 ml of the seed culture was inoculated into the medium and incubated at 24° C. for 20 hours with aeration at 10 l/min. and stirring at 125 rpm. After incubation, the culture was centrifuged to obtain a culture supernatant. The culture supernatant was concentrated to a volume of 400 ml using an ultrafiltration instrument equipped with hollow fibers having an exclusion molecular weight of 10,000 to obtain a solution of fucoidan-degrading enzyme.

(2) 600 ml of a solution containing fucoidan derived from Kjellmaniella crassifolia at a concentration of 5%, 750 ml of 100 mM phosphate buffer (pH 8.0), 150 ml of 4 M sodium chloride and 120 ml of the fucoidan-degrading enzyme solution prepared in Referential Example 3-(1) were mixed together and reacted at 25° C. for 144 hours.

The reaction mixture was dialyzed using a dialysis membrane having a pore size of 3500 to collect a fraction containing substances each having a molecular weight of 3500 or less. The fraction was desalted using Microanalyzer G3 (Asahi Kasei), and 500 ml of desalted solution was obtained. The desalted solution was applied to DEAE-Sepharose FF column (5 cm×26 cm) (Pharmacia) equilibrated with 10 mM ammonium acetate. Elution was carried out with 1 l of 10 mM ammonium acetate, 1 l of a gradient of ammonium acetate concentration from 10 mM to 1 M, 1 l of 1 M ammonium acetate, and 1 l of a gradient of ammonium acetate concentration from 1 M to 5 M in this order. Eluate was collected at the rate of 50 ml per fraction. Fraction numbers 64 to 78 were collected, concentrated to a volume of 200 ml, desalted and applied to DEAE-Sepharose FF column (2.4 cm×22 cm) equilibrated with 500 mM ammonium acetate. Elution was carried out with 100 ml of 500 mM ammonium acetate and 900 ml of a gradient of ammonium acetate concentration from 500 mM to 2 M in this order. Eluate was collected at the rate of 9.7 ml per fraction. Fraction numbers 92 to 96 were collected, concentrated and desalted to obtain the compound of formula (II) (hereinafter simply referred to as 6-5s).

Example 1

Production and cloning of hybridoma cell producing anti-fucoidan monoclonal antibody (1) 100 $\mu$g of the fucoidan derived from Kjellmaniella crassifolia as an antigen prepared as described in Referential Example 1-(1) was mixed and emulsified with Freund's complete adjuvant in a volume of 100 $\mu$l, and then intraperitoneally administered to each of four 6-weeks old female Balb/c mice (Clea Japan).

21 days after the priming, 100 $\mu$g of the same fucoidan as that used for the priming was mixed and emulsified with Freund's incomplete adjuvant in a volume of 100 $\mu$l, and then intraperitoneally administered to each of the mice for boosting.

14 days after the boosting, 100 $\mu$g of the same fucoidan as that used for the priming was intraperitoneally administered to each of the mice in a volume of 100 $\mu$l for auxiliary immunization.

3 days after the auxiliary immunization, a spleen was removed from each mouse and slowly dispersed to homogeneity in 10 ml of RPMI 1640 medium (Bio Whittaker) using a stainless mesh. Spleen cells were isolated by repeating centrifugation at 1500 rpm and washing three times.

The thus-obtained spleen cells were centrifuged and combined with washed mouse myeloma P3U1 (P3X63AgU.1) cells. 1 ml of a PEG 1500 solution (RPMI 1640 medium containing polyethylene glycol (PEG) at a concentration of 50% (v/v)) was added dropwise to the mixture over 1 minute. After further mixing for 1 minute, the mixture was slowly diluted with RPMI 1640 medium to make the PEG concentration become 5% (v/v).

Cells were separated by centrifugation and dispersed by slowly adding thereto a proliferation medium (RPMI 1640 medium containing 10% fetal calf serum (FCS)). $10^6$ of the cells in a volume of 0.1 ml were seeded into each well of a 96-well culture plate (Falcon). The plate was incubated at 37° C. overnight in a 5% $CO_2$ incubator.

On the next day, 100 $\mu$l of a selective medium prepared by adding 0.1 mM hypoxanthine, 0.4 $\mu$M aminopterin and 16 $\mu$M thymidine to the proliferation medium (hereinafter referred to as HAT medium) was added to each well. Incubation was continued while replacing the medium with 100 $\mu$l of fresh HAT medium at intervals of 1 or 2 days, i.e., under selective conditions in which non-fused cells were killed and only fused cells could survive.

Furthermore, anti-fucoidan monoclonal antibodies contained in culture supernatants were detected with enzyme immunoassay when colonies became large in order to select lines positive for antibody production among survival fused cells.

The concentration of fucoidan, which was used as the antigen for the immunization, was adjusted to 10 µg/ml with phosphate buffered saline (PBS). 50 µl of the dilution was added to each well of a 96-well microtiter plate (Nunc). The plate was allowed to stand at 4° C. overnight for immobilization.

After immobilization, the fluid was discarded and 200 µl of a commercially available blocking agent (Block Ace, Dainippon Pharmaceutical) was added to each well. The plate was incubated at 37° C. for 2 hours for blocking to prepare a plate having the antigen being immobilized.

50 µl each of culture supernatants from the respective fused cells was added to the plate. The plate was incubated at 37° C. for 1 hour to effect antigen-antibody reactions.

The plate was washed with PBS. 50 µl of a 1000-fold dilution of horse radish peroxidase (HRP)-labeled anti-mouse IgG antibody (Zymed) with the blocking agent was added to each well. The plate was incubated at 37° C. for 1 hour.

The plate was washed with PBS. 50 µl of an ABTS/0.02% hydrogen peroxide solution (0.1 M citrate-sodium hydroxide buffer (pH 4.0) containing 2,2'-azino-bis(3-ethylbenzothiazoline-6-sulfonic acid) diammonium salt (ABTS, Nacalai Tesque) at a concentration of 0.55 mg/ml, and 0.02% hydrogen peroxide) was added to each well. The plate was incubated at room temperature for 15 minutes for color development.

A well that developed green color was judged positive. The positive lines were expanded by transferring the colonies from the 96-well plate to a 24-well plate, then to a 6-well plate in HT medium (HAT medium without aminopterin). Cloning was carried out by limiting dilution as follows. The expanded cells were diluted with a commercially available cloning medium (S-Clone, Sanko Junyaku) such that each well of a 96-well culture plate contained one cell. The dilution was then seeded to the 96-well plate and the cells were incubated.

Culture supernatants from grown single colonies were subjected to enzyme immunoassay using a plate having fucoidan as an antigen being immobilized in order to detect positive lines.

As a result, two monoclonal antibody-producing cell clones, GFD 2-9C and GFD G-28 were obtained. These cells have been deposited on Oct. 29, 1996 (the date of the original deposit) at the National Institute of Bioscience and Human-Technology, Agency of Industrial Science and Technology, Ministry of International Trade and Industry, 1-3, Higashi 1-chome, Tsukuba-shi, Ibaraki-ken, Japan under accession numbers FERM BP-7174 (GFD 2-9C) and FERM BP-7173 (GFD G-28).

(2) Each of the cloned monoclonal antibody-producing cells was grown in a proliferation medium (RPMI 1640 medium containing 10% fetal calf serum (FCS)), and then $10^6$ to $10^7$ of the cells were intraperitoneally implanted into a Balb/c mouse which had received 0.5 ml of an immunosuppressive agent, pristane (2,6,10,14-tetramethylpentadecane, Wako Pure Chemical Industries), 3 weeks before. Monoclonal antibodies were purified from accumulated ascites collected after 2 weeks.

(3) The ascites collected from the abdominal cavity of each mouse was centrifuged at 3000 rpm for 10 minutes to remove precipitates. The supernatant was diluted twice with PBS and filtrated through cotton. The thus-obtained filtrate was subjected to salting out with 50% ammonium sulfate to precipitate the antibody, and then centrifuged.

The resulting precipitate was dissolved in PBS. The solutions w as dialyzed against PBS to remove ammonium sulfate, and then subjected to affinity treatment using Protein A column (Pharmacia) according to a conventional method.

The column was equilibrated with a Protein A adsorption buffer (3M NaCl, 1.5 M glycine, pH 8.9). The dialyzed solution containing the antibody, which was prepared by dissolving the precipitate, was treated with the Protein A column. The adsorbed fraction was washed with the Protein A adsorption buffer, and then eluted with 0.1 M citrate buffer (pH 4.0).

The eluted fraction was dialyzed against PBS. When the thus-obtained dialysate was subjected to sodium dodecyl sulfate-polyacrylamide gel electrophoresis (hereinafter referred to as SDS-PAGE), it was confirmed to result in a single band. Thus, a purified antibody was obtained.

The anti-fucoidan antibodies produced by the hybridomas GFD 2-9C and GFD G-28 were designated as GFD2-9C and GFDG-28, respectively.

(4) The subclasses of the anti-fucoidan antibodies were determined by enzyme immunoassay using commercially available rabbit anti-mouse IgG1, IgG2a, IgG2b, IgG3 and IgM polyclonal antibodies (Zymed).

The concentration of purified fucoidan, which was used as the antigen for the immunization, was adjusted to 10 µg/ml with PBS. 50 µl of the dilution was added to each well of a 96-well microtiter plate (Nunc). The plate was allowed to stand at 4° C. overnight for adsorption.

The fluid in the plate was discarded, the plate was washed with PBS, and each well was blocked by adding thereto 200 µl of the commercially available blocking agent (Block Ace, Dainippon Pharmaceutical) to prepare an antigen plate.

The concentration of each of the purified anti-fucoidan antibodies GFD2-9C and GFDG-28 was adjusted to 10 µg/ml with the commercially available blocking agent (Block Ace, Dainippon Pharmaceutical). 50 µl each of the dilutions was added to the plate. The plate was incubated at 37° C. for 1 hour for reaction.

The plate was washed with PBS. 50 µl each of 1000-fold dilutions of commercially available rabbit anti-mouse IgG1, IgG2a, IgG2b, IgG3 and IgM polyclonal antibodies (Zymed) with the commercially available blocking agent (Block Ace, Dainippon Pharmaceutical) was added to each well. The plate was incubated at 37° C. for 1 hour for reaction.

The plate was washed with PBS. 50 µl of a 500-fold dilution of a commercially available HRP-labeled anti-rabbit secondary antibody (Zymed) with the commercially available blocking agent (Block Ace, Dainippon Pharmaceutical) was added to each well. The plate was incubated at 37° C. for 1 hour for reaction.

The plate was washed with PBS. 50 µl of the ABTS/0.02% hydrogen peroxide solution was added to each well. The plate was incubated at room temperature for 15 minutes for color development.

As a result, it was demonstrated that both of the antibodies were of the IgG1 subclass.

(5) The fucoidan-derived compounds, 7-12s and 6-5s, were used to conduct competitive tests with fucoidan derived from *Kjellmaniella crassifolia*.

The concentration of purified fucoidan derived from *Kjellmaniella crassifolia* was adjusted to 10 µg/ml with PBS. 50 μl of the solution was added to each well of a 96-well microtiter plate (Nunc). The plate was allowed to stand at 4° C. overnight for immobilization. Blocking was carried out using 200 μl of the commercially available blocking agent (Block Ace, Dainippon Pharmaceutical) to prepare an antigen plate.

The concentration of the enzymatically degraded saccharide fragment solutions were adjusted to 1 mg/ml with distilled water. Three 3-fold serial dilutions (3-, 9- and 27-fold) were prepared with the commercially available blocking agent (Block Ace, Dainippon Pharmaceutical) for each of solutions above. Competitive solutions including these dilutions as well as a solution that contained only the blocking agent and did not contain 7-12s or 6-5s were dispensed to 1.5-ml Eppendorf tubes (Eppendorf).

Antibody solutions were prepared by adjusting the concentrations of the anti-fucoidan antibodies GFD2-9C and GFDG-28 to 10 μg/ml with the commercially available blocking agent (Block Ace, Dainippon Pharmaceutical).

50 μl of one of the solutions containing the antibody GFD2-9C or GFDG-28 at a concentration of 10 μg/ml was added to 50 μl of one of the competition -solutions (containing 7-12s or 6-5s at the defined concentration, or only the blocking agent). The mixtures were incubated at 37° C. for 30 minutes to prepare primary reaction mixtures.

In the primary reaction, if the binding site in the antibody GFD2-9C or GFDG-28 is occupied upon the binding reaction with 7-12s or 6-5s in the competitive solution (i.e., if a binding site for the antibody is present in 7-12s or 6-5s), in a secondary reaction, the binding ability of the antibody to an immobilized antigen on a plate is lost in proportion to the concentration of 7-12s or 6-5s.

For the secondary reaction, 50 μl each of the respective primary reaction mixtures was added to the plate having fucoidan derived from *Kjellmaniella crassifolia* as an antigen being immobilized. The plate was incubated at 37° C. for 1 hour.

After washing the plate three times with PBS, 50 μl of a 500-fold dilution of the HRP-labeled anti-mouse secondary antibody with the commercially available blocking agent (Block Ace, Dainippon Pharmaceutical) was added to each well. The plate was incubated at 37° C. for 1 hour.

After washing the plate four times with PBS, 50 μl of the ABTS/0.02% hydrogen peroxide solution was added to each well. The plate was incubated for 15 minutes for color development.

The reaction was stopped by adding 50 μl of 150 mM oxalic acid to each well, and the absorbance at 405 nm was measured using a plate reader.

That is to say, if the color development is decreased in proportion to the concentration of 7-12s or 6-5s in the competitive solution, it is considered that a binding site for the antibody is present in 7-12s or 6-5s.

As a result, it was demonstrated that the anti-fucoidan antibody GFD2-9C binds to 6-5s and does not bind to 7-12s, and that GFDG-28 binds to 7-12s and does not bind to 6-5s as shown in Table 1 below.

TABLE 1

| Antibody clone | Compound | Competitive compound concentration (μg/ml) | | | |
| --- | --- | --- | --- | --- | --- |
| | | 333 | 111 | 36.7 | 0 |
| | | Absorbance measured at 405 nm | | | |
| GFD2-9C | 6-5s | 0.160 | 0.235 | 0.277 | 0.293 |
| | 7-12s | 0.294 | 0.281 | 0.318 | 0.305 |
| GFDG-28 | 6-5s | 0.364 | 0.385 | 0.405 | 0.400 |
| | 7-12s | 0.194 | 0.345 | 0.373 | 0.418 |

(6) A HRP-labeled antibody was prepared according to the method as described in P. K. Nakane, "Immunoassays in the Clinical Laboratory", pp. 81, Alan R. Liss Inc. (1979).

10 mg of HRP (Boehringer-Mannheim) was dissolved in 1 ml of distilled water. 0.2 ml of 0.1 M sodium periodate was added thereto. The mixture was reacted at room temperature for 20 minutes, and then dialyzed against 1 mM sodium acetate buffer (pH 4.0) overnight.

The pH of the resulting solution was adjusted to 9 to 9.5 by adding 0.02 ml of 2 M sodium carbonate buffer (pH 9.5). One of the monoclonal antibodies GFD2-9C and GFDG-28, which had been dialyzed against 0.01 M sodium carbonate buffer (pH 9.5), was added to the dialyzed solution above at a final concentration of 10 mg/ml. The mixtures were reacted at room temperature for 2 hours. 0.1 ml of sodium boron hydride (4 mg/ml) was then added to each mixture, and the resulting mixtures were reacted at 4° C. for 2 hours.

The reaction mixtures were dialyzed against PBS at 4° C. overnight. Thus, HRP-labeled GFD2-9C and HRP-labeled GFDG-28 were obtained.

The concentration of the antibody GFD2-9C or GFDG-28 was adjusted to 10 μg/ml with PBS. 50 μl of one the solutions was added to each well of a 96-well microtiter plate (Nunc). The plate was allowed to stand at 4° C. overnight to immobilize the antibodies.

The fluid in each well of the plate was discarded, and 200 μl of the commercially available blocking agent (Block Ace, Dainippon Pharmaceutical) was added to each well. The plate was incubated at 37° C. for 1 hour for blocking to prepare an immobilized plate.

50 μl each o f 5-fold serial dilutions of a solution containing 6-5s at a concentration of 40 μg/ml (the top (maximal) concentration) for the measurement system using GFD2-9C, or 3-fold serial dilutions of a solution containing 7-12s at a concentration of 111 μg/ml (the top concentration) for the measurement system using GFDG-28 was added as a standard (hereinafter referred to as STD) to the plate. The plate was incubated at 37° C. for 1 hour for reaction.

After reaction, the plate was washed three times with PBS. 50 μl of 500-fold dilution of the HRP-labeled GFD2-9C or the HRP-labeled GFDG-28 with the commercially available blocking agent was added to each well. The plate was incubated at 37° C. for 1 hour for reaction.

After reaction, the plate was washed four times with PBS. 50 μl of the ABTS/0.02% hydrogen peroxide solution was added to each well. The plate was incubated at room temperature for 15 minutes for color development.

The absorbance at 405 nm was measured for each well using a plate reader. The results are shown in Table 2.

Calibration curves were prepared based on the absorbance measured with 6-5s (for GFD2-9C) or 7-12s (for GFDG-28) as STD.

As a result, the measured absorbance value was increased in proportion to the concentration of 6-5s or 7-12s as shown in Table 2 below. These results show that the sandwich enzyme immunoassay (sandwich EIA) measurement system functions well.

TABLE 2

| Immobilized antibody GFD2-9C | | | HRP-labeled antibody GFD2-9C | | | STD 6-5s |
|---|---|---|---|---|---|---|
| Absorbance measured at 405 nm 5-fold serial dilutions starting from top concentration (40 µg/ml) | | | | | | |
| Top 1.687 | 0.870 | 0.264 | 0.111 | 0.062 | 0.073 | 0.058 |
| Immobilized antibody GFDG-28 | | | HRP-labeled antibody GFDG-28 | | | STD 7-12s |
| Absorbance measured at 405 nm 3-fold serial dilutions starting from top concentration (111 µg/ml) | | | | | | |
| Top 1.589 | 0.780 | 0.316 | 0.150 | 0.087 | 0.066 | 0.042 |

Fucoidan derived from *Kjellmaniella crassifolia* could be measured in a sandwich EIA measurement system using a combination of GFD2-9C and the HRP-labeled GFDG-28. The results are shown in Table 3 below. In addition, a combination of GFD2-9C and the HRP-labeled GFD2-9C, a combination of GFDG-28 and the HRP-labeled GFDG-28, and a combination of GFDG-28 and the HRP-labeled GFD2-9C were examined respectively. As a result, it was found that fucoidan derived from *Kjellmaniella crassifolia* could be measured in a sandwich EIA measurement system using these combinations. Furthermore, it was found that F-fucoidan could be measured in a sandwich EIA measurement system using a combination of GFDG-28 and the HRP-labeled GFDG-28.

TABLE 3

| Immobilized antibody GFD2-9C | | | HRP-labeled antibody GFDG-28 | | | STD Fucoidan from *Kjellmaniella crassifolia* |
|---|---|---|---|---|---|---|
| Absorbance measured at 405 nm 5-fold serial dilutions starting from top concentration (40 µg/ml) | | | | | | |
| Top 0.449 | 0.220 | 0.139 | 0.089 | 0.086 | 0.073 | 0.072 |

Example 2
Preparation of Anti-fucoidan Antibody Column

HiTrap NHS-activated column (Pharmacia) was washed with 6 ml of 1 mM hydrochloric acid. 0.9 ml of the GFDG-28 solution purified in Example 1-(3) was applied to the column. After allowing to stand at room temperature for 1 hour, the column was washed with 3 ml of a coupling buffer (0.5 M sodium chloride, 0.2 M sodium bicarbonate, pH 8.3). Next, the column was washed with 6 ml of a blocking buffer (0.5 M Tris-hydrochloride (pH 8.3), 0.5 M sodium chloride), 6 ml of a buffer B (0.1 M sodium acetate (pH 4.0), 0.5 M sodium chloride) and 6 ml of the blocking buffer in this order, and then the column was allowed to stand at room temperature for 30 minutes. The column was further washed with 6 ml of the buffer B, 6 ml of the blocking buffer and 6 ml of the buffer B, and then the column was equilibrated with PBS to prepare an anti-fucoidan antibody column.

A solution obtained by dissolving purified fucoidan derived from *Kjellmaniella crassifolia* in PBS was applied to the anti-fucoidan antibody column. When the eluate was subjected to DEAE-Cellulofine A-800 column chromatography as described in Referential Example 1-(2), no peak was observed for fractions corresponding to the salt concentration at which F-fucoidan is eluted using a sodium chloride gradient. Thus, it was found that F-fucoidan could be removed from fucoidan derived from *Kjellmaniella crassifolia* by using the column in which GFDG-28 was immobilized. Furthermore, when an eluate obtained with an immobilized GFD2-9C column was treated as described in Referential Example 3-(2), 6-5s could not be obtained after DEAE-Sepharose FF column chromatography. Thus, it was found that 6-5s and polysaccharides containing 6-5s could be removed.

As described above, by using the antibody of the present invention, various materials having compounds that bind to the antibody GFD2-9C or GFDG-28 in their structures can be detected and quantified.

INDUSTRIAL APPLICABILITY

The present invention provides an anti-fucoidan antibody that specifically binds to the structure of fucoidan, which is useful for the structural analysis and the quantification of fucoidan.

The relationship between the structure and the physiological functions of fucoidan is revealed using the antibody. Thus, such an antibody is very useful in the field of biochemistry. Furthermore, fucoidan having a physiologically functional structure can be selected from ones of various origins. In addition, the antibody can be used to purify fucoidan of interest.

What is claimed is:
1. An anti-fucoidan antibody, which is produced by hybridoma GFD G-28 (FERM BP-7173).
2. An anti-fucoidan antibody, which is produced by hybridoma GFD 2-9C (FERM BP-7174).

* * * * *